(12) United States Patent
Rotering

(10) Patent No.: US 11,872,247 B2
(45) Date of Patent: Jan. 16, 2024

(54) COMBINATION OF A WOUND-RINSING SOLUTION AND COLD PLASMA FOR THE TREATMENT OF WOUNDS

(71) Applicant: Westfaelische Wilhelms-Universitaet Muenster, Münster (DE)

(72) Inventor: Heinrich Rotering, Havixbeck (DE)

(73) Assignee: Westfaelische Wilhelms-Universitaet Muenster, Muenster (DE)

( * ) Notice: Subject to any disclaimer, the term of this patent is extended or adjusted under 35 U.S.C. 154(b) by 0 days.

(21) Appl. No.: 16/964,873

(22) PCT Filed: Jan. 24, 2019

(86) PCT No.: PCT/EP2019/051680
§ 371 (c)(1),
(2) Date: Jul. 24, 2020

(87) PCT Pub. No.: WO2019/145383
PCT Pub. Date: Aug. 1, 2019

(65) Prior Publication Data
US 2021/0030596 A1    Feb. 4, 2021

(30) Foreign Application Priority Data
Jan. 26, 2018  (DE) ..................... 10 2018 101 748.0

(51) Int. Cl.
*A61K 33/44* (2006.01)
*A61F 13/00* (2006.01)
*A61M 1/00* (2006.01)

(52) U.S. Cl.
CPC ........ *A61K 33/44* (2013.01); *A61F 13/00068* (2013.01); *A61M 1/85* (2021.05);
(Continued)

(58) Field of Classification Search
CPC ...... A61F 13/00068; A61F 2013/00187; A61F 13/00063; A61F 2013/00536; A61M 1/90;
(Continued)

(56) References Cited

U.S. PATENT DOCUMENTS 8,267,884 B1    9/2012  Hicks
2002/0150720 A1*  10/2002  Howard ................. A61M 1/77
428/131

(Continued)

FOREIGN PATENT DOCUMENTS

DE    102014002000 A1    8/2015
EP    2206521 A1    7/2010

OTHER PUBLICATIONS

Zorflex Wound Contact Dressings (Changes, Opportunities and Challenges: Wound Management in Changing Healthcare Systems, EWMA Journal, vol. 16, No. 2, Nov. 2016). (Year: 2016).*

(Continued)

*Primary Examiner* — Ariana Zimbouski
(74) *Attorney, Agent, or Firm* — Kagan Binder PLLC

(57) ABSTRACT

The present invention relates to the use of a combination of a wound-rinsing solution and cold atmospheric plasma for treating wounds. The present invention further relates to a method for treating wounds, comprising rinsing the wound with a wound solution and treating the wound with cold atmospheric plasma.

8 Claims, 3 Drawing Sheets

(52) U.S. Cl.
CPC .............. *A61M 1/915* (2021.05); *A61M 1/92* (2021.05); *A61F 2013/00187* (2013.01); *A61M 2202/0208* (2013.01); *A61M 2202/0415* (2013.01)

(58) Field of Classification Search
CPC .. A61M 2202/0208; A61M 2202/0415; A61M 35/30; A61M 1/85; A61M 3/0204; A61M 2202/025; A61M 2205/051; A61M 1/915; A61M 1/92; A61M 1/94; A61M 1/77; A61K 33/00; A61K 45/06; A61K 33/44; A61L 2/0094; A61L 2/14; A61L 15/18; A61L 15/42; A61N 5/0624
See application file for complete search history.

(56) References Cited

U.S. PATENT DOCUMENTS

| | | | | |
|---|---|---|---|---|
| 2012/0046602 | A1* | 2/2012 | Morfill | A61L 2/0011 604/23 |
| 2015/0165182 | A1* | 6/2015 | Pratt | A61M 1/92 604/290 |
| 2015/0320604 | A1* | 11/2015 | Adie | A61F 13/022 604/319 |
| 2017/0189349 | A1* | 7/2017 | Roe | A61N 1/44 |
| 2019/0110933 | A1 | 4/2019 | Weltmann et al. | |

OTHER PUBLICATIONS

Eswaramoorthy et al. (2017) "Plasma treatments of dressings for wound healing: a review", Biophys. Rev., 9:895-917.

Emmert et al. (2012) "Treatment of Chronic Venous Leg Ulcers with a Hand-Held DBD Plasma Generator", Plasma Medicine, 2:19-32.

Kammerlander, G., et al. (2011) "A clinical evaluation of the efficacy and safety of singlet oxygen in cleansing and disinfecting stagnating wounds", Journal of Wound Care 28:149-158.

Isbary, G., et al. (2012) "Successful and safe use of 2 min cold atmospheric argon plasma in chronic wounds: results of a randomized controlled trial", British Association of Dermatology, 167:404-410.

Rotering, H. (2016) "Advanced NPWT for infected wounds in long-term implants", Vivano Spectrum, Convincing case examples of negative-pressure wound therapy, Published by Paul Hartmann AG, pp. 1-6.

* cited by examiner

A

B

C

COMBINATION OF A WOUND-RINSING SOLUTION AND COLD PLASMA FOR THE TREATMENT OF WOUNDS

CROSS REFERENCE TO RELATED APPLICATIONS

This application claims priority to International Application No. PCT/EP2019/051680, filed on Jan. 24, 2019, which claims the benefit of German Application No. 10 2018 101 748.0, filed Jan. 26, 2018, the content of which is incorporated by reference in its entirety.

The present invention relates to the use of a combination of a wound-rinsing solution and cold atmospheric plasma for treating wounds. The present invention further relates to a method for treating wounds, comprising rinsing the wound with a wound solution and treating the wound with cold atmospheric plasma.

Many wounds, especially chronic wounds, heal very slowly or not at all. Serious infections, often caused by bacteria, are frequently responsible for this, which can no longer or barely be controlled with antibiotics because of resistance.

Large, externally accessible and often chronic wounds are treated with wound-rinsing solutions to clean the wound. On the one hand, tissue residues, necrosis particles, excess exudate, deposits, dressing residues, cell debris, etc. are removed, and biofilms—often together with antiseptics and surgical debridement—are also removed.

Such wound-rinsing solutions are generally isotonic (physiological) and can contain various antiseptics which, depending on where they are used and the cause of the infection, comprise bactericidal, bacteriostatic, fungicidal, fungistatic and/or virucidal active substances. Some wound rinsing-solutions also comprise reactive oxygen such as singlet oxygen, which may be initially complexed (e.g. sodium hypochlorite) and then released (Kammerlander et al., pro care August 2012, pp. 26-29). However, not all wounds can be healed with wound-rinsing solutions, and there are often recurrences after treatment.

The present invention addresses this technical problem as set forth in the present description and as defined in the claims.

DRAWINGS

DESCRIPTION

Figure 1:
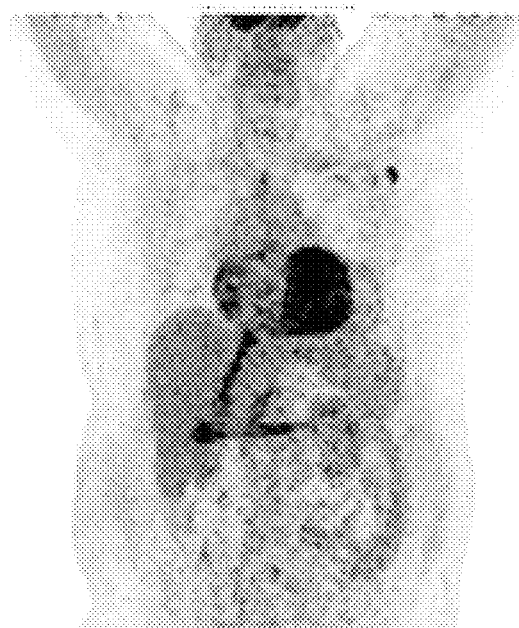
FIG. 1A shows the patient described in Example 4 before treatment of the wound according to the invention. The patient had an infected driveline.
FIG. 1B shows a PET/CT image of the patient described in Example 4 before treatment of the wound according to the invention. The patient had an infected driveline.
FIG. 1C shows the patient described in Example 4 after 3 weeks of treatment of the wound according to the invention.
Figure 1:
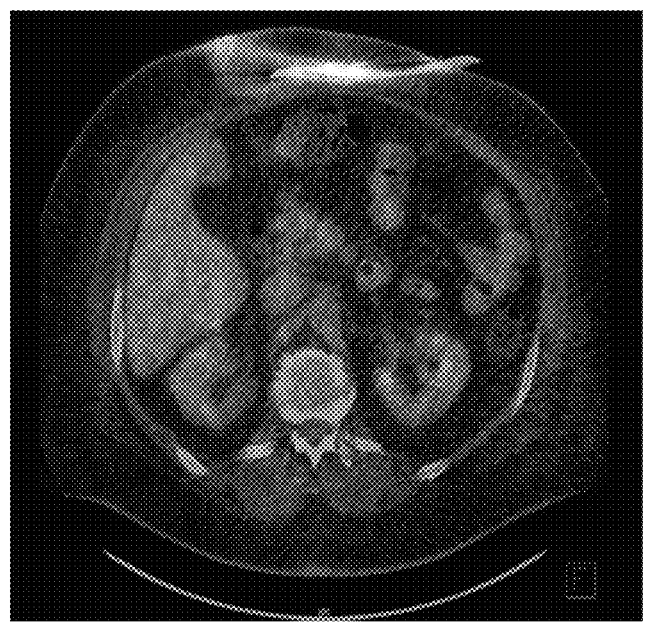
Figure 1:
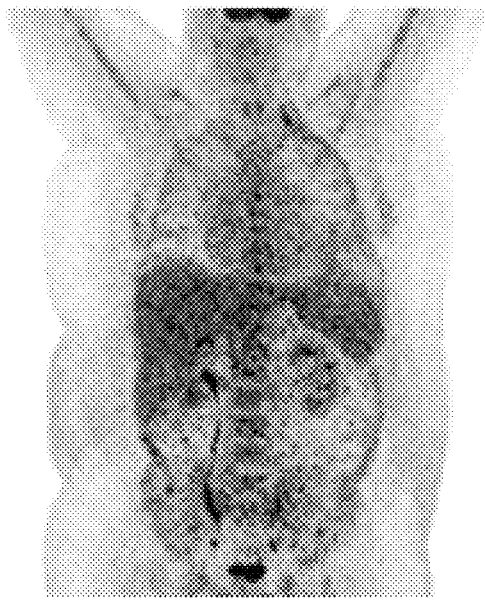

As was surprisingly found in the context of the present invention, a combination of a wound-rinsing solution with cold atmospheric plasma (hereinafter also referred to as "cold plasma" or "CAP") is very well suited for use in treating wounds. As could be shown, chronic wounds can be largely treated and the number or intensity of recurrences can be significantly reduced. No undesirable side effects were observed. It was found that treating wounds with a wound-rinsing solution alone, for example ActiMaris®, did not lead to satisfactory success, whereas the combination of a wound-rinsing solution and cold plasma led to more than satisfactory, in this case surprising, therapeutic success in the treatment of wounds.

The present invention therefore relates to the use of a combination of a wound-rinsing solution and cold atmospheric plasma for treating wounds.

Alternatively, the present invention relates to the use of a combination of a wound-rinsing solution and cold atmospheric plasma for use in treating wounds.

In one embodiment of the present invention, an activated carbon dressing is also used for the treatment of wounds, preferably a vacuum activated carbon dressing. Examples of suitable activated carbon dressings are known to the person skilled in the art and include, inter alia, Actisorb®, Askina® Carbosorb, CarboFlex®, Vliwaktiv® AG absorbent compress, and others. A dressing composed of activated carbon and a vacuum sponge can be used as a vacuum activated carbon dressing, as is known to the person skilled in the art, for example, as "advanced negative pressure wound therapy (aNPWT) or activated carbon NPWT. When using activated carbon NPWT (aNPWT), intensive wound therapy with more frequent changes (every 2 to 3 days) is possible, since the carbon film ensures active cleaning. The release of oxygen radicals is expressly desired with this use.

The aNPWT treatment method is, however, to be distinguished from the NPWT standard method from the prior art, for example Avance®Flex (Molnlycke®). This involves the use of a green sponge, which enables the detection of blood loss by discoloration of the sponge. This method from Molnlycke Health Care expressly discourages the use of hypochlorite solution and hydrogen peroxide due to the release of oxygen radicals. It is simply a modified NPWT procedure (use of a green sponge), but without an activated carbon dressing in the sense of wound cleaning as used with aNPWT.

When using activated carbon NPWT, the activated carbon can also fix residual germs under the vacuum sponge and thus reduce a renewed progression of the infection. According to the invention, the progress of treatment can thus be further supported by the combination of a wound-rinsing solution and cold atmospheric plasma. In the application according to the invention, an activated carbon dressing is particularly preferred, in which the activated carbon-containing part is applied (i.e. placed) directly onto the wound. This allows bacteria to be bound without a barrier. A preferred activated carbon dressing, which enables a direct application of the activated carbon-containing part of the dressing, is Zorflex® activated carbon (Chemviron (England)). So far, no company has recommended the carbon film in direct contact with the wound bed.

The present invention further relates to a method for treating wounds, comprising
 (a) rinsing the wound with a wound solution, and
 (b) treating the wound with cold atmospheric plasma.

A moist film of the rinsing solution preferably remains in the wound bed before the wound is treated with cold atmospheric plasma.

In one embodiment of the present invention, the method can also comprise a further step:

(c) repeated rinsing of the wound with a wound-rinsing solution (preferably with the same wound-rinsing solution as in step (a)) and/or (d) applying an activated carbon dressing to the wound.

According to the invention, steps (a), (b) and optionally (c) and/or (d) are preferably carried out in the order (a), (b), ((c), (d)).

The method according to the invention can additionally comprise a further step of treating the wound-rinsing solution with cold atmospheric plasma, preferably prior to step (a) and/or prior to step (c).

In connection with step (d), it is preferably a vacuum activated carbon dressing according to the invention. Examples of suitable (vacuum) activated carbon dressings are known to the person skilled in the art, as already explained above.

The present invention alternatively relates to a combination of a wound-rinsing solution and cold atmospheric plasma for use in a method for treating wounds, comprising (a) rinsing the wound with a wound solution, and (b) treating the wound with cold atmospheric plasma.

A moist film of the rinsing solution preferably remains in the wound bed before the wound is treated with cold atmospheric plasma.

In one embodiment of the present invention, the combination of a wound-rinsing solution and cold atmospheric plasma described above for use in a method for treating wounds may also comprise a further step:

(c) repeated rinsing of the wound with a wound-rinsing solution (preferably with the same wound-rinsing solution as in step (a)) and/or (d) applying an activated carbon dressing to the wound.

According to the invention, steps (a), (b) and optionally (c) and/or (d) are preferably carried out in the order (a), (b), ((c), (d)).

In one embodiment of the present invention, the combination of a wound-rinsing solution and cold atmospheric plasma described above for use in a method for treating wounds may also comprise the further step of treating the wound-rinsing solution with cold atmospheric plasma, preferably prior to step (a) and/or prior to step (c).

In connection with step (d), it is preferably a vacuum activated carbon dressing according to the invention. Examples of suitable (vacuum) activated carbon dressings are known to the person skilled in the art, as already explained above.

In this respect, the present invention alternatively also relates to a combination of a wound-rinsing solution and cold atmospheric plasma for use in treating wounds, wherein the wound-rinsing solution is designed for rinsing wounds and the cold atmospheric plasma is designed for treating wounds.

A moist film of the rinsing solution preferably remains in the wound bed before the wound is treated with cold atmospheric plasma.

Furthermore, in one embodiment, the present invention alternatively also relates to a combination of a wound-rinsing solution, cold atmospheric plasma and an activated carbon dressing for use in treating wounds, wherein the wound-rinsing solution is designed for rinsing wounds, the cold atmospheric plasma injection is designed for treating wounds and an activated carbon dressing is prepared for application to the wound.

Wound-rinsing solutions in connection with the present invention in particular include solutions that are suitable for wound cleaning and can be adapted to the wound to be rinsed or cleaned, as is known to the person skilled in the art.

In one embodiment, these are wound-rinsing solutions that are sterile, painless or almost painless, physiological, non-irritating or corrosive, and/or can be heated to at least 28° C. Wound-rinsing solutions in connection with the present invention can include salts (e.g. NaCl, sea salt) and/or electrolytes (e.g. sodium, potassium, calcium), alcohols (e.g. ethanol, isopropanol, phenoxyethanol), quaternary ammonium compounds (e.g. benzalkonium, cetylpyridinium, octenidine, polyhexanide), iodine-containing compounds (e.g. povidone iodine/PVP iodine), chlorine-containing compounds (e.g. chlorhexidine), hexetidine, bibrocathol, taurolidine, enzymes (e.g. varidase, fibrolan), and/or (further) bactericidal, bacteriostatic, fungicidal, fungistatic, and/or virucidal ingredients (antiseptics). Such bactericidal, bacteriostatic, fungicidal, fungistatic, and/or virucidal ingredients can include, for example: antibiotics, reactive compounds such as ROS (reactive oxygen species) and/or RNS (reactive nitrogen species). Examples of ROS in this context include singlet oxygen ($^1O_2$), oxygen radicals, hydrogen peroxide ($H_2O_2$), ozone (O3) and others. Examples of RNA include NO and $NO_2$. According to the invention, ROS as a potential component of wound-rinsing solutions can also be complexed in other compounds, for example singlet oxygen in the form of sodium hypochlorite (NaOCl). In the case of complexed singlet oxygen such as NaOCl, the singlet oxygen is then generally released on contact with the wound, as is known to the person skilled in the art. In one embodiment of the present invention, the wound-rinsing solution contains approximately 0.01-0.1% by weight NaOCl, preferably approximately 0.01-0.08, approximately 0.02-0.08, approximately 0.02-0.07, approximately 0.02-0.06 or approximately 0.02-0.05 or 0.03-0.05% by weight NaOCl.

In one embodiment of the present invention, the wound-rinsing solution contains singlet oxygen ($^1O_2$), which, as already described, also includes complexed singlet oxygen ($^1O_2$), such as sodium hypochlorite (NaOCl). With complexed singlet oxygen such as NaOCl, the singlet oxygen is usually released upon contact with the wound. In one particular embodiment, the wound-rinsing solution also contains salt, for example NaCl, and/or sea salt. In one particular embodiment, the salt content (for example NaCl content) is below 5, preferably 4 or 3% by weight of the wound-rinsing solution. In a further embodiment of the present invention, the wound-rinsing solution contains polyhexanide and/or octenidine, preferably polyhexanide. Suitable wound-rinsing solutions are known to the person skilled in the art and can be tailored to the wound to be treated. In the context of the present invention, the wound-rinsing solution can be, for example, ActiMaris®, Lavanox®, Kerrasol®, BIOsept® wound-rinsing solution, or Microdacyn60® Wound Care, preferably ActiMaris®, Lavanox® or Kerrasol®, and particularly preferably Lavanox® or Kerrasol®.

The wounds to be treated according to the invention can in principle be all types of wounds which are accessible to a wound-rinsing solution and treatment with cold plasma. These are preferably wounds on the skin or mucous membrane, which are preferably accessible without surgery (superficial wound). In one embodiment of the present invention, the wound to be treated is infected or inflamed with one or more bacteria and/or viruses, preferably bacteria. Typical bacterial infections and inflammations can be caused by, for example, *Enterobacter* sp. (e.g. *E. cloacae*), *Pseudomonas* sp. (e.g. *P. aeroginosa*), *Staphylococcus* sp. (e.g. *S. aureus*), *Klebsiella* sp. (e.g. *K. pneumonia*), *E. coli*, *Streptococcus* sp., and/or *Proteus* sp. In one embodiment, the wound to be treated according to the invention is acutely or chronically infected or inflamed, preferably chronically (chronic wound). "Chronic" in this context can mean that the wound has not healed within at least 4, 6 or 8 weeks after the wound has developed, preferably after at least 4 weeks.

In connection with the present invention, the wound to be treated is treated using a combination of a wound-rinsing solution as shown here and cold (also referred to as "non-thermal") atmospheric plasma (also referred to as "cold plasma" here). Cold atmospheric plasma (cold plasma) comprises partially ionized gas (for example ambient air, argon, helium mixtures, preferably with a low admixture of oxygen, or nitrogen; preferably argon), which is generated under atmospheric conditions (ambient pressure). The plasma temperature preferably does not exceed 50° C., preferably not 40° C. In one embodiment, only up to 0.1 to 10 ppb (parts per billion) of ionized particles are present in cold plasma, for example 0.5 to 5 ppb or approximately 1 ppb. In the context of the present invention, cold plasma can generate electrons, ions, radicals, ROS, RNS and/or UV radiation. The generation and use of cold plasma are known to the person skilled in the art, for example as offered by terraplasma medial GmbH (Germany; http://terraplasma-medical.com/). Typical gases for plasma generation according to the invention may include, inter alia: air, argon, helium mixtures, preferably with a small admixture of oxygen, and/or nitrogen, preferably argon. Devices according to the invention for generating and using cold plasma and for use in medical treatment are known to the person skilled in the art and include, for example, PlasmaDerm® (Cinogy), kINPen® (INP Greifswald), Plasma One (plasma Medical Systems GmbH) and SteriPlas® (Adtec Healthcare). Cold plasma can in principle be used in any suitable manner as is known to the person skilled in the art and as described, for example, in Eswaramoorthy et al., Biophys (2017), 9: 895-917.

As already described, the wound is first rinsed with a suitable wound-rinsing solution in connection with the present invention. The exposure time can vary depending on the wound and is typically approximately 5 to 10 minutes, preferably approximately 7 to 8 minutes. Depending on the accessibility of the wound, the wound-rinsing solution can be applied directly or with aids such as soaked compresses. Likewise, within the scope of the present invention, infected areas in the vicinity of the wound, which are not themselves part of the wound but which could favor renewed infection of the wound (e.g. cables, tubes, implants or other devices), can be treated with the wound-rinsing solution. The wound-rinsing solution can then be removed as far as possible using suitable measures (e.g. compresses). In one embodiment of the present invention, the wound-rinsing solution is not completely dried off, so that a residual moisture content is retained. It is also possible according to the invention to treat the remaining wound-rinsing solution with cold plasma in addition to the wound or the areas close to the wound in the subsequent step of cold plasma treatment. Thereafter, according to the invention, the wound and optionally, where appropriate, the above-mentioned infected areas in the vicinity of the wound are treated with cold atmospheric plasma. The treatment is carried out depending on the wound, as is readily apparent to those skilled in the art. Relevant parameters include the size and depth of the wound and, where appropriate, the degree of infection. A typical treatment time with cold plasma can also be approximately 5 to 10 minutes, preferably approximately 3 to 5 minutes; in the case of larger wounds, such as sternum wounds, as a rule, 5 to 10 minutes. After plasma treatment, a further step of wound rinsing can then take place, analogously to the first wound rinsing, wherein preferably the same wound-rinsing solution is used in both cases. In one embodiment of the present invention, after plasma treatment, there is a further step of rinsing with a wound-rinsing solution, preferably with the same wound-rinsing solution as in the previous rinsing. Thereafter, the wound-rinsing solution can again be removed as far as possible by means of suitable measures (e.g. compresses).

In one embodiment of the present invention, the wound-rinsing solution itself can also be treated with cold plasma, for example for approximately 5 to 10 minutes, or approximately 3 to 5 minutes. This can be the case in particular if the wound-rinsing solution has not been completely dried off after rinsing the wound, as already described above.

After treating the wound with cold plasma or after subsequent rinsing with the wound-rinsing solution as shown in the context of the present invention, the wound can also be treated with an activated carbon dressing for the treatment of wounds, preferably with a vacuum activated carbon dressing (advanced negative pressure wound therapy (aNPWT)). Examples of suitable activated carbon dressings are known to the person skilled in the art and include, inter alia, Actisorb®, Askina® Carbosorb, CarboFlex®, Vliwaktiv® AG absorbent compress, and others. A dressing composed of activated carbon and a vacuum sponge can be used as a vacuum activated carbon dressing, as is known to the person skilled in the art, for example, as "advanced negative pressure wound therapy" (aNPWT). The activated carbon can fix residual germs under the vacuum sponge and thus reduce a renewed progression of the infection. According to the invention, the progress of treatment can thus be further supported by the combination of a wound-rinsing solution and cold atmospheric plasma. In the application according to the invention, an activated carbon dressing is particularly preferred, in which the activated carbon-containing part is applied (i.e. placed) directly onto the wound. This allows bacteria to be bound without a barrier. A preferred activated carbon dressing, which enables a direct application of the activated carbon-containing part of the dressing, is Zorflex® activated carbon (Chemviron (England)).

In the context of the present invention, the singular form always includes the corresponding plural form, unless explicitly stated otherwise.

Furthermore, the expression "and/or" includes both the respective terms "and" and "or", as well as all or any possible combination of the respective elements which are connected by "and/or".

The term "approximately" preferably means within 20%, 10%, 5% or 2% within the corresponding value or range. In addition, the exact values or ranges that follow the term "approximately" are expressly included.

The term "comprising" as used herein means the inclusion of the respective features, terms or values, but not the exclusion of features, terms or values not listed. An embodiment of the term "comprising" can also represent the exclusive term "consisting of", unless explicitly stated otherwise.

It should be understood that this invention is not limited to the particular methods, protocols, materials, reagents and substances, etc. described herein, and as such may vary. The terminology used here is used only to describe certain embodiments and is not intended to limit the scope of the present invention, which is defined solely by the claims.

All publications and patents cited in this description (including all patents, patent applications, scientific publications, manufacturer information, instructions, etc.), whether above or below, are hereby incorporated in their entirety by reference. Nothing herein should be construed as a concession that the invention is not authorized to anticipate such disclosure based on a previous invention. Insofar as the material referred to contradicts or is incompatible with this description, the description itself replaces this material.

The following examples serve only to illustrate the present invention and in no way limit the object of the invention. The object of the present invention is defined by the claims.

EXAMPLES

Example 1

General Treatment Regimen

Surgical treatment of a wound may be required before starting therapy. The wound area is opened as completely as possible. General surgical debridement is performed. Avital tissue and bone parts are removed if necessary. This serves as a first reduction of the germ load and prepares the wound bed. After sufficient hemostasis has been achieved, a first dressing (activated carbon NPWT) can be applied.

The combination therapy according to the invention is usually carried out in the outpatient department. Thanks to this less painful procedure, analgesics or even anesthesia standby can generally be dispensed with. Dressing changes are carried out under sterile conditions (sterile gloves, work surfaces, face masks). For this reason, two people are optimally required to carry out this therapy quickly and safely.

Example 2

Rinsing and Cold Plasma Treatment of Wounds

Wound Rinsing to Release Singlet Oxygen in the Wound

After removing the surgical dressing (photo documentation, taking swabs), the wound area is rinsed with a wound-rinsing solution with activated oxygen (e.g. ActiMaris, Kerrasol, Lavanox). In the event that there are external accesses to the inside of the body, for example driveline, the sections to be treated are wrapped with appropriately soaked compresses. The exposure time is on average 5 to 8 minutes. The excess liquid is then removed with dry compresses so that a moist film of the rinsing solution remains in the wound bed.

Cold Plasma Treatment

The wound area to be treated is treated with cold plasma (e.g. SteriPlas by Adtec). Argon plasma is generated from argon gas in an electric field, which in turn forms the reactive oxygen species (ROS) from atmospheric oxygen. Together with a low proportion of UV light, these form the effective components for combating pathogens and for stimulating the body's own cells to better fight infection. In addition to the direct plasma effect (high penetration depth resulting from atomic structure), the remainder of the rinsing liquid extends the so-called plasma action time. The cold plasma exposure time is approximately 5 minutes per treated area section (i.e. 8 to 10 minutes with an open sternum, for example).

Example 3

Wound Rinsing with Activated Oxygen, Cold Plasma Treatment and Wound Sealing with Activated Carbon NPWT Repeated Wound Rinsing with the Release of Singlet Oxygen Immediately after cold plasma treatment, the wound bed is treated as thoroughly as possible with the rinsing solution (if necessary, wet compresses for external access, e.g. driveline). This is done on the one hand to utilize the available treatment time, but also to protect the wound bed from contamination until the sealing dressing is applied. The exposure time, which is approximately another 5 minutes, is used to prepare the activated carbon NPWT dressing in the last treatment step. Immediately before inserting the activated carbon film, the liquid is removed with dry compresses.

Applying the Activated Carbon NPWT Dressing (aNPWT)

Figure 2:
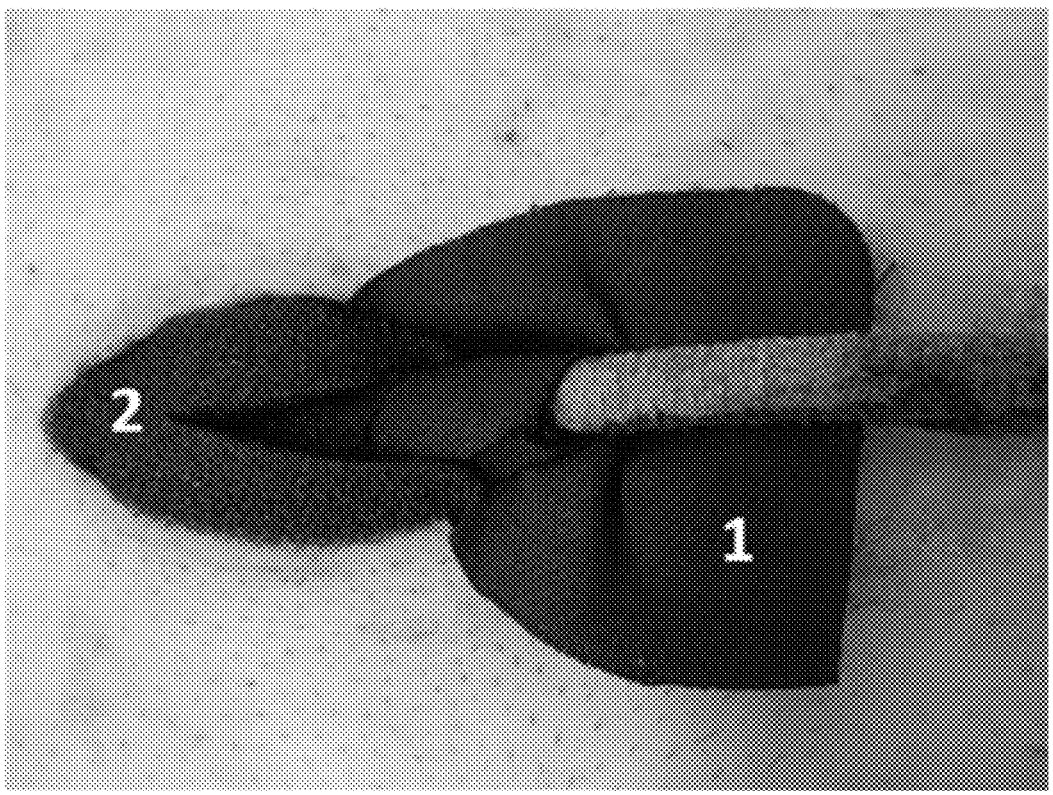
FIG. 2 shows a driveline with activated carbon NPWT dressing: an activated carbon film (1) is placed in the wound bed, envelops the driveline and protrudes from the wound to cover the surrounding skin area; a gray-black NPWT sponge (2) is placed over the activated carbon film.

The NPWT sponge is cut on a sterile pad. The activated carbon film is placed in the wound bed. It should be noted here that the film fills the entire wound bed if possible (one or two layers) in order to make the best possible surface contact with the wound tissue. The carbon film should protrude from the wound to cover the surrounding skin area for 1 to 2 cm (protection of wound edges to prevent pathogen migration). The customized NPWT sponge is then inserted and taped with a sealing film (FIG. 2). In the case of deep sternal infections, a double-layer application of film and sponge is also possible: first a layer of activated carbon to protect the heart, then an intersternal sponge, then activated carbon for the presernal soft tissue and finally a superficial sponge.

Change Intervals

Figure 3:
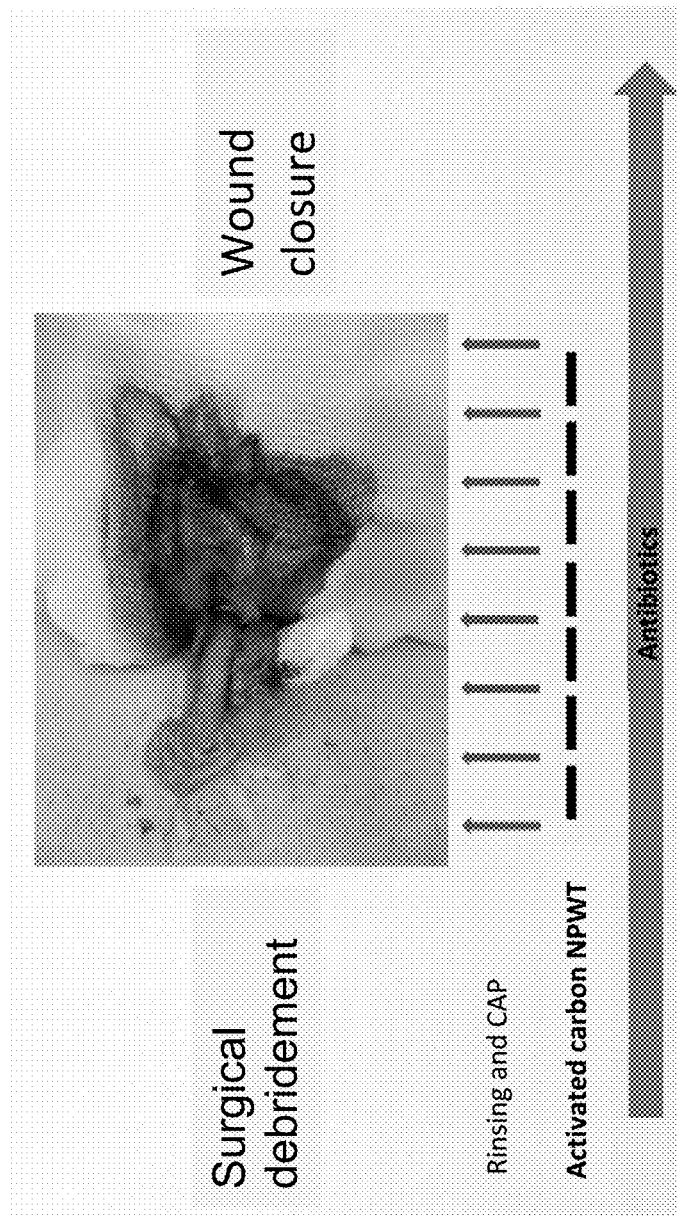
FIG. 3 shows the alternation of rinsing and cold plasma (CAP) and the sealing of the wound with activated carbon NPWT.

The goal of intensified wound treatment is to shorten the therapy time, which should ultimately reduce the risk for the patient (wound complications) and help to save costs over the long term. For these reasons, it is necessary to shorten the change intervals (FIG. 3). While time intervals of 4 to 5 days were normal for the usual treatment with standard NPWT, a dressing change with cold plasma application should be carried out every 2 to 3 days under this treatment regimen. The shortened change intervals prevent regeneration of the pathogens in the NPWT period being made significantly more difficult, especially since fresh active substances (especially singlet oxygen) are applied with each treatment. The activated carbon film in the sealed wound inhibits the migration of pathogens and thus helps to isolate possible residual sources of infection more quickly.

Completion of Treatment

After consolidation of the wound bed (result of swab analysis, inflammation values (e.g. CRP course), macroscopic findings, granulation), the wound is closed. Treatment with a rinsing solution and cold plasma can optionally be repeated, including in the OR.

Example 4

The patient received an artificial heart (LVAD) in 2013. From fall 2015, he was initially in outpatient treatment for driveline infection. The first documented driveline treatment with ActiMaris took Place®. A few months later, inpatient admission was required for operative remediation of the infection. The finding was so pronounced that odor of the *Pseudomonas* infestation could be detected before the patient entered through the door. The degree of infection is shown in FIGS. 1A and 1B. Operative revision was carried out immediately. After the bleeding tendency subsided, the patient was treated with the combination method according to the invention. The infection parameters normalized within only three weeks (CRP<0.5) (see FIG. 1C) and the patient was discharged with the wound into outpatient care at his own request.

It should be noted that treatment with ActiMaris Alone® was unsuccessful for more than six months, so that the infection progressed significantly with an increase in the infection parameters. After three weeks of combination therapy, the improvement in findings shown above could be achieved with normalization of the infection values.

The invention claimed is:

1. A method for treating wounds, comprising the following steps in the order of:
   (a) rinsing the wound with a wound-rinsing solution,
   (b) treating the wound with cold atmospheric plasma, and
   (c) applying a vacuum activated carbon dressing to the wound.

2. The method according to claim 1, further comprising repeated rinsing of the wound with a wound-rinsing solution.

3. The method according to claim 1, further comprising treating the wound-rinsing solution remaining on the wound with cold atmospheric plasma.

4. The method according to claim 1, wherein the wound-rinsing solution contains reactive oxygen.

5. The method according to claim 1, wherein the wound-rinsing solution contains singlet oxygen.

6. The method according to claim 1, wherein ambient air or argon is used for plasma generation.

7. The method according to claim 1, wherein the salt content of the wound-rinsing solution is less than 4% by weight.

8. The method according to claim 1, further comprising a step of rinsing the wound between step (b) and step (c) with a wound-rinsing solution that is the same as the wound-rinsing solution of step (a) or that is a wound-rinsing solution different than step (a).

* * * * *